United States Patent [19]

Rickwood et al.

[11] Patent Number: 5,446,150
[45] Date of Patent: Aug. 29, 1995

[54] PHOTOCHROMIC SPIROXAZINE COMPOUNDS

[75] Inventors: Martin Rickwood, Southport; Sean D. Marsden, St. Helens; Victoria E. Askew, Upminster, all of United Kingdom

[73] Assignee: Pilkington plc, St. Helens, United Kingdom

[21] Appl. No.: 160,173

[22] Filed: Dec. 2, 1993

[30] Foreign Application Priority Data

Dec. 3, 1992 [GB] United Kingdom ............... 9225346

[51] Int. Cl.$^6$ ............................................ C07D 265/14
[52] U.S. Cl. ......................................... 544/71; 252/586
[58] Field of Search ......................................... 544/71

[56] References Cited

U.S. PATENT DOCUMENTS

| | | | |
|---|---|---|---|
| 4,913,544 | 4/1990 | Rickwood et al. | 351/163 |
| 4,931,219 | 6/1990 | Kwiatkowski et al. | 252/586 |
| 4,968,454 | 11/1990 | Crano et al. | 252/586 |
| 5,017,698 | 5/1991 | Machida et al. | 544/71 |

FOREIGN PATENT DOCUMENTS

| | | |
|---|---|---|
| 0146135 | 6/1985 | European Pat. Off. . |
| 0141407 | 6/1988 | European Pat. Off. . |
| 0294056A2 | 12/1988 | European Pat. Off. . |
| 0245020B1 | 10/1991 | European Pat. Off. . |
| 0449669A1 | 10/1991 | European Pat. Off. . |
| 2049297 | 3/1971 | France . |
| 4076087 | 3/1992 | Japan . |
| 1310918 | 3/1973 | United Kingdom . |
| 1515641 | 6/1978 | United Kingdom . |
| 1515642 | 6/1978 | United Kingdom . |
| 2190088 | 12/1989 | United Kingdom . |
| WO85/02619 | 6/1985 | WIPO . |
| WO87/00524 | 1/1987 | WIPO . |

OTHER PUBLICATIONS

European Search Report, EP 93 30 9417, dated Feb. 23, 1994.
C. B. McArdle, "*Applied Photochromic Polymer Systems*", 1992, Chapter 2, pp. 33–34.
Alan R. Katritzky and Kunihiko Akutagawa, "*A Practical Synthetic Method for N–Methyl-o-Toluidine*", OPPI Briefs, vol. 21, No. 3, 1989, pp. 340–341.
Alan R. Katritzky, Stanislaw Rachwal and Bogumila Rachwal, "*The Chemistry of Benzotriazole, Part 3.*[1] *The Aminoalkylation of Benzotriazole*", J. Chem. Soc. Perkin Trans. 1, 1987, pp. 799–804.
Louis F. Fieser, "*β–Naphthoquinone and α–Naphthoquinone*", Organic Synthesis 1937, 17, pp. 68–72.
Katsuhira Yoshida, Tetsunao Koujiri, Norio Oga, Miwa Ishiguro and Yuji Kubo, "*The Effect of Metal Chelate Complexation on The Reactivity and Absorption Spectra of 1,2–Naphthoquinones: The Synthesis of New Types of Near I.r. Absorbing Dyes*", J. Chem. Soc., Chem. Commun., 1989, pp. 708–710.
Marshall Gates, "*The Condensation of Naphthoquinones With Polar Ethylenes*", from the Marian Edwards Park Laboratory of Bryn Mawr College, Jan. 1944, vol. 66, pp. 124–130.

Primary Examiner—Mukund J. Shah
Assistant Examiner—Matthew V. Grumbling
Attorney, Agent, or Firm—Burns, Doane, Swecker & Mathis

[57] ABSTRACT

Photochromic materials which have a structure which includes a spiro-pyrrolidinebenzoxazine structure comprising a pyrrolidine part and a benzoxazine part and the benzoxazine part includes at least one mesomeric electron donating group chosen from amino and alkoxy moieties, the one or more mesomeric electron donating groups being linked to the 6' position via attachment to a conjugated system in which the unsaturated bonds forming the linkage are chosen from —C=C—, —C≡C—, —C=N— and —N=N—.

20 Claims, No Drawings

PHOTOCHROMIC SPIROXAZINE COMPOUNDS

The present invention relates to photochromic compounds and articles such as ophthalmic lenses and windows including vehicle rooflights made From polymeric material in which the compounds are incorporated to confer photochromic properties on the polymeric material.

U.S. Pat. No. 4,913,544 describes a group of photochromic compounds capable of darkening to a dense colour which belong to the class of compounds known as spiro-oxazines. The compounds disclosed in this specification darken to a blue or purple colour, and exhibit an unexpected denser colouring in their darkened state than previously known organic photochromic compounds.

Typical of the compounds with these properties disclosed in U.S. Pat. No. 4,913,544 is a compound of the formula:

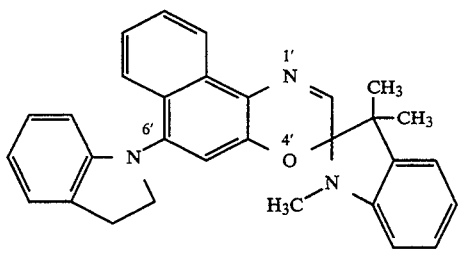

These compounds have an amino functionality substituted at the 6' position.

In the manufacture of windows for both glazing buildings and vehicles, a desirable property is the ability to absorb in the infra-red and thus control the transmission of heat through the window. We have now Found by extending the chromophore structures of the compounds of the type disclosed in U.S. Pat. No. 4,913,544, it is possible to manufacture compounds which exhibit a pleasing green colour in the darkened state and may also have a useful infra red absorbance in the near inFra red region circa 780 nm in that state.

One way the chromophore structure may be extended is by synthesising compounds in which there is no longer a group with an amino functionality directly substituted at the 6' position in the spiro-benzoxazine structure, but at least one group with amine functionality is still present but linked to the 6' position through a conjugated system.

An alternative way of obtaining a similar result is to use an alkoxy substituent separated From the 6' position in the spiro-benzoxazine structure by a conjugated system. We believe that these substituents act as mesomeric electron donating groups in the ring open or darkened state.

According to the invention, there are provided new photochromic compounds characterised in that they have a structure which includes a spiro-pyrrolidinebenzoxazine structure comprising a pyrrolidine part and a benzoxazine part and the benzoxazine part includes at least one mesomeric electron donating group chosen from amino and alkoxy moieties, the one or more mesomeric electron donating groups being linked to the 6' position via attachment to a conjugated system in which the unsaturated bonds forming the linkage are chosen from —C=C—, —C≡C—, —C=N— and —N=N—.

New photochromic compounds are also included in our invention in which the conjugated system includes at least one aromatic or heterocyclic ring.

The new photochromic compounds according to the invention can have a structure where the pyrrolidine part is annulated with a carbocyclic ring chosen From benzene and naphthalene and the structures are respectively spiroindolino benzoxazine and spirobenzindolinobenzoxazine. The pyrrolidine part may be annulated with a heterocyclic moiety. The benzoxazine portion can contain a carbocyclic or heterocyclic moiety fused at the 7' and 8' position. A bridge may be established between the $N_1$ position on the pyrolidine and part of the annulated moiety.

The preferred photochromic compounds according to the invention have the structure of formula I

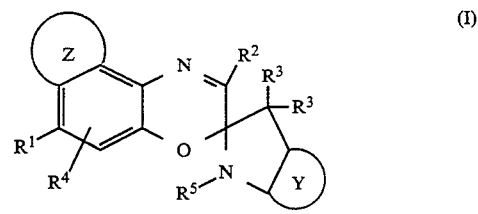

wherein $R^1$ is a group selected from an aryl, heteroaryl, heterocyclic, alkenyl, alkenylaryl, cycloalkenyl, cycloalkenylaryl, alkynyl, alkynylaryl, iminoaryl and azoaryl forming a linkage to at least one amino or alkoxy group;

$R^2$ is a group selected from hydrogen, alkyl, alkoxy, aryl, heteroaryl or amino;

$R^3$ are independent and are selected from C1 to C10 branched or linear alkyls, carbocyclic or heterocyclic rings or together form part of a carbocyclic or heterocyclic ring;

$R^4$ is a group selected from hydrogen, alkyl, alkoxy, alkenyl alkynyl, imino, azo, amino, carboxy ester, amide, cyano, halogen, trifluoromethyl, nitro, aryl or heteroaryl.

$R^5$ is a group selected From C1 to C20 alkyls either branched, linear or alicyclic, alkenyl, alkynyl, alkoxyalkyl, carbocyclic, alkylcarbocyclic, heterocyclic or alkylheterocyclic.

Z when present represents a carbocyclic or heterocyclic moiety; and

Y when present is a six membered carbocyclic or heterocyclic moiety.

Further preferred photochromic compounds have a structure as shown in Formula II:

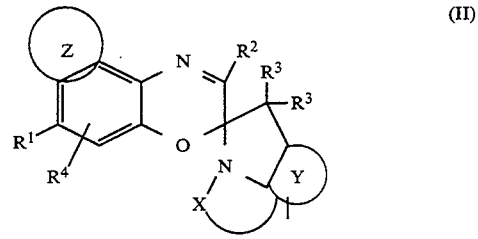

wherein $R_1$, $R_2$, $R_3$, $R_4$, Z and Y are as defined above, and X forms a heterocyclic moiety.

Particularly preferred photochromic compounds have the structure shown in formula III

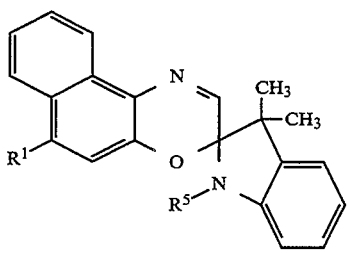

(III)

where R₁ is selected from

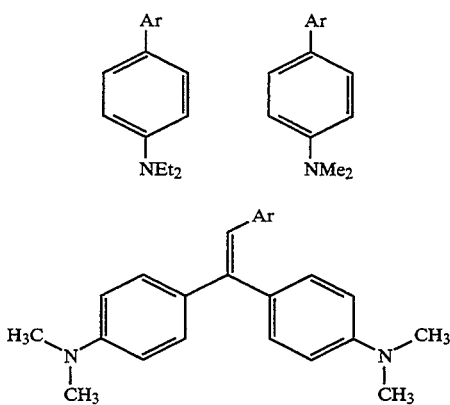

where Ar indicates the point of attachment to the oxazine part of the structure, and R₅ is selected From C1–C18 linear or branched alkyls, such as methyl, ethyl, isobutyl and neopentyl.

Compounds having the structure shown in formula IV may also be made.

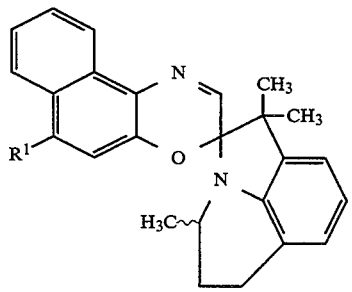

(IV)

where R₁ is as defined in above.

In the above description of the present invention the numbering of the atom centre in the compounds is not strictly in accordance with the standard adopted worldwide, i.e. IUPAG or Chemical Abstracts. For reason of maintaining the above description on manageable (understandingwise) terms the compounds have all been numbered so that the nitrogen of oxazine moiety has always been designated as 1'.

In a majority of cases, for example, the napthoxazines this is in line with the IUPAC system. However, in some cases, for example, strict benzoxazine compounds the approach adopted varies from IUPAC.

In the manufacture of these compounds, we have found it necessary to synthesise certain novel materials as intermediates. These materials are 1-nitroso-2-hydroxynapthalene derivatives and are formed by reacting a naphthoquinone derivative with hydroxylamine hydrochloride or acid salt of hydroxylamine such as hydroxylamine-o-sulphonic acid.

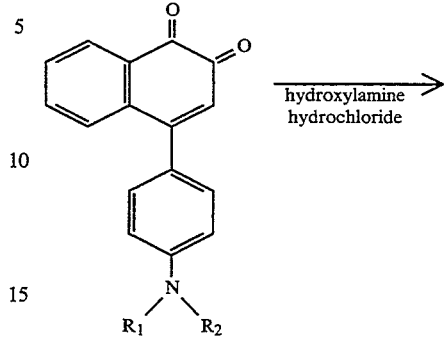

wherein:

R₁ and R₂ are each selected From the group consisting of alkyl containing 1 to 4 carbon atoms, alkylalkoxy, hydroxylicalkyl containing 1 to 4 carbon atoms, aryl and carboyclic or R₁ to R₂ together form part of a heterocyclic grouping or at least one of R₁ and R₂ form part of a heterocyclic grouping fused with the phenyl group to which the NR₁R₂ group is attached. Desirably, at least one of R₁ and R₂ is phenyl or cyclohexyl or R₁ and R₂ jointly form a piperidine group or the NR₁,R₂ group is

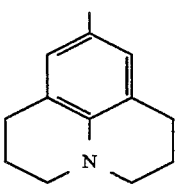

The napthoquinone starting materials are known, and their synthesis has been described in J. Chem. Soc., Chem. Commun., 1989, 708–710 JACS, 1944, 66, 125–130 Organic Synthesis 1937, 17, 68

Examples 1, 2 and 3 below illustrate the route to the spiroxazine compounds of the present invention. Examples 4 to 9 were made by the same route.

The photochromic spiro-oxazines of the present invention may be dispersed in a solid polymer matrix without losing their photochromic properties.

Examples of suitable plastics host materials are optically clear plastics selected from polymers of polyol(allyl carbonate)-monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, poly(styrene methylmethacrylate) coopolymers, poly(styrene acrylonitrile) copolymers, and polyvinylbutyral. Transparent copolymers and blends of the transparent polymers are also suitable as host materials.

Preferably, the host material is an optically clear polymerized organic material such as triethylene glycol dimethacrylate (TEGDM) or a material sold under the trade name CR-39, namely diethylene glycol bis(allyl carbonate).

The photochromic spiro-oxazine compounds of Formula (I) may be applied to or incorporated in the plastic host material by any of the conventional methods known in the art, for example by the methods exemplified in European Patent Specification No. 141407. Typically, such methods include dissolving or dispersing the photochromic compound in the host material. The photochromic compound may be dispersed into the host by "imbibition", i.e. diffusion of the photochromic compound into the host material by a suitable transfer mechanism such as immersion, thermal transfer or vapour phase transfer.

Typically a plastic lens is Formed by using a conventional direct casting process in which the polymerisable composition incorporating the photochromic spiro-oxazine compound is introduced into a mould and is then cured by heating. Suitable curing conditions are, For example, heating at a temperature ranging From room temperature to 100° C., generally over a period of about 5 hours. A typically curing schedule is to subject the material to be cured to a temperature beginning at 40° C. rising up to a temperature in the range 80°–90° C. over a period of about 5 hours.

The amount of the photochromic compound incorporated into the plastic host material is usually of the order of From 0.05% to 5% by weight, based on the volume of the host material. However, the amount of photochromic compound is not critical and can be varied depending upon the method which is used to apply or incorporate the photochromic compound. In particular, when the spiro-oxazine compound is applied to or imbibed into the surface of the article, the amount used will usually be significantly less than 0.05% by weight.

Articles in accordance with the present invention typically exhibit a pale colouration in the faded condition, dependent on the nature of the compound used and a green colour in the darkened condition.

If desired, the colour of the article can be modified with conventional water-based dyes or tints. For example, it is possible to make an article which is grey or brown in its faded condition and darkens to a blue/grey colouration when exposed to sunlight.

The following examples illustrate but do not limit the invention.

EXAMPLE 1

1,2-naphthoquinone-4-sulphonic acid sodium salt (13.0 g;0.05 mol) was dissolved in 10% aqueous methanol (300 ml) by stirring at room temperature. The mixture was treated with N,N-diethylaniline (7.45 g;0.05 mol) and the solution stirred for 5 hours at room temperature.

The reaction was filtered and the collected dark solid washed with a small quantity of water and air dried to give 4-(p-diethylamino)phenyl-1,2-naphthoquinone (shown below) (12.9 g;85%) as a dark blue solid.

M.Pt.160°–196° C.(Decomp.)

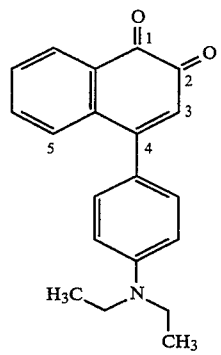

4-(p-diethylamino)phenyl-1,2-naphthoquinone (4.7 g;0.015 mol) was dissolved in absolute ethanol (250 ml) stirred at room temperature and treated with hydroxylamine hydrochloride (2.09 g;0.03 mol). After 1 hour the mixture was filtered to yield 4-(p-diethylamino)phenyl-1-nitroso-2-hydroxynaphthalene (2.67 g;56%) as a red-brown solid.

M.Pt.201°–204° C.

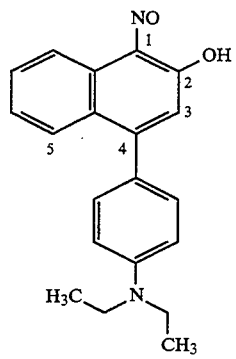

A solution of 4-(p-diethylamino)phenyl-1-nitroso-2-hydroxynaphthalene (0.85 g; 0.0027 mol) and 1,3-dihydro-1,3,3-trimethyl-2-methyleneindoline (0.5 g; 0.0029 mol) in methanol (60 ml), under nitrogen, was heated under reflux for 24 hours. The solution was then evaporated and chromatographed over silica (1 part diethyl ether to 10 parts pet. ether) to afford 1,3-dihydro-1,3,3-trimethyl-6′-(p-diethylamino)phenylspiro[2H-indole-2,3′-[3H]naphth[2,1-b],[1,4] oxazine](0.47 g;36%) as a yellow solid (Formula V).

M.Pt.157°–8°

Absorbance; $\lambda_{max}$ 626nm (Polyurethane)

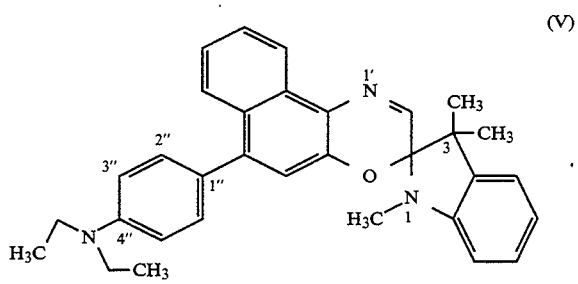

(V)

EXAMPLE 2

1,2-naphthoquinone-4-sulphonic acid sodium salt (13.0 g;0.05 mol) was dissolved in 10% aqueous methanol (300 ml) by stirring at room temperature. The mixture was treated with N,N-dimethylaniline (7.45 g;0.062 mol) and the solution stirred for 4 hours at room temperature.

The reaction was filtered and the collected dark solid washed with a small quantity of water and air dried to give 4-(p-dimethylamino) phenyl-1,2-naphthoquinone (shown below) (12.92 g;93%) as a dark blue solid.

M.Pt 181°-84° C.

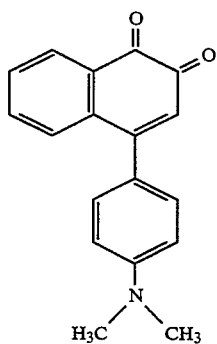

4-(p-dimethylamino)phenyl-1,2-naphthoquinone(12.9 g;0.047 mol) was dissolved in absolute ethanol (300 ml), stirred at room temperature and treated with hydroxylamine hydrochloride (6.58 g;0.094 mol). After 1 hour the mixture was filtered to yield 4-(p-dimethylamino)-phenyl-1,2-naphthoquinone (shown below) (7.47 g 59%) as a red-brown solid.

M.Pt 201°-207° C.

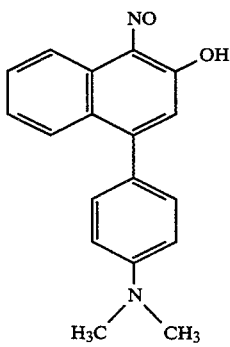

A solution of 4-(p-dimethylamino)phenyl-1-nitroso-2-hydroxynaphthalene(0.70 g;0.0024 mol) and 1,3-dihydro-3,3-dimethyl-1-neopentyl-2-methyleneindoline (0.46 g;0.002 mol) in methanol (60 ml) was heated under nitrogen and reflux for 48 hours. The solution was then evaporated and chromatographed over silica (1 party diethyl ether to 5 parts pet. ether) to afford 1,3-dihydro-3,3-dimethyl-1-neopentyl-6'-(p-dimethylamino)phenyl-spiro[2H-indole-2,3'-[3H]naphth[2,1-b][1,4]oxazine](0.47 g;36%) as a yellow solid (Formula VI).

mp 198°-202° C.

Absorbance: λ$_{max}$ 626 nm (PU)

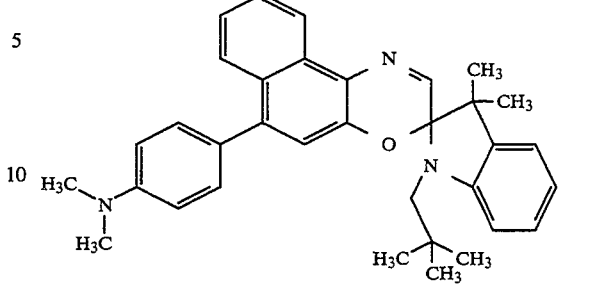

(VI)

EXAMPLE 3

1,2-naphthoquinone (4.74 g;0.03 mol) dissolved in warm methanol (50 ml) was stirred and treated with 1,1-bis-(p-dimethylamino)phenylethylene (3.89 g;0.015 mol). The resulting blue-green solution was heated to reflux for 5 min. and then allowed to cool and stand at room temperature For 18 hours. Filtration afforded 2-(1,2-naphthoquinon-4-yl)-1,1-bis(p-dimethylaminophenyl)ethylene (3.93 g;64%) as a dark blue solid.

M.Pt 197° C. decomp. (lit.* 199°-201° C.)

* M. Gates, J. Amer. Chem. Soc., 1944,66,124-130

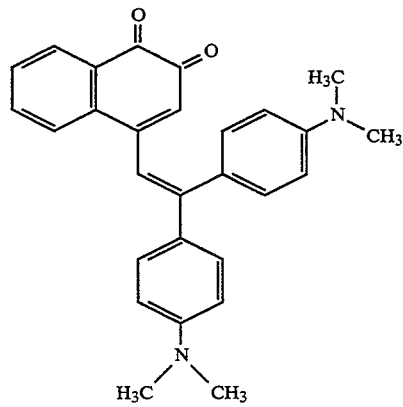

2-(1,2-naphthoquinon-4-yl)-1,1-bis(p-dimethylaminophenyl)ethylene (1.63 g; 0.004 mol) was dissolved in absolute ethanol (100 ml) by warming. To the solution, at room temperature, was added hydroxylamine hydrochloride (3.7 g;0.053 mol) and the resulting solution was stirred for 5 hours. The mixture was then evaporated to dryness treated with water and extracted with CH$_2$Cl$_2$. The organic extract was dried, evaporated to dryness and then chromatographed over silica (eluent:diethyl ether) to afford 2-(1-nitroso-2-hydroxynaphthalen-4-yl)-1,1-bis(p-dimethylamin ophenyl)ethylene (0.83 g;49%) as a dark brown solid.

M.Pt 186° decomp.

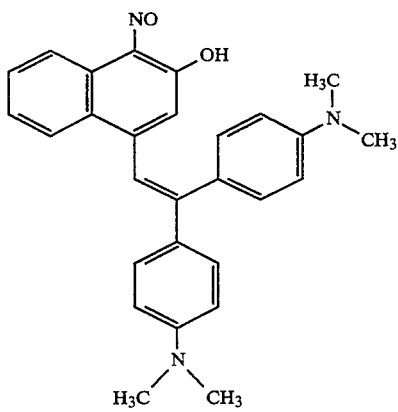

A solution of 2-(1-nitroso-2-hydroxynaphthalen-4-yl)-1,1-bis(p-dimethylaminophenyl)ethylene (4.0 g; 0.009 mol) 1,3-dihydro-1,3,3-trimethyl-2-methyleneindoline (1.73 g; 0.010 mol) in methanol (30 ml) was heated under reflux and nitrogen for 6 hours. The resulting solution was evaporated to dryness and chromatographed over silica (1 part diethyl ether to 5 parts of pet. ether) to afford 1,3-dihydro-1,3,3-trimethyl-6′-(1,1-bis[p-dimethylaminophenyl]ethylen-2-yl)spiro[2H-indole-2,3′-[3H]naphth[2,1-b][1,4]oxazine](0.92 g;17%) as a green solid (Formula VII).

Absorbance: $\lambda_{max}$ 656 nm(PU)

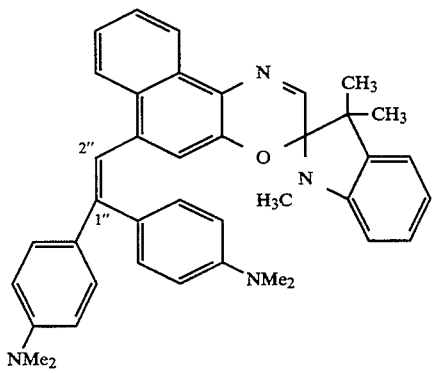

(VII)

EXAMPLES 4–9

The compounds listed below as examples 4–9 were made by a process analogous to that described in Examples 1, 2 or 3; and the melting points obtained.

EXAMPLE 4

1,3-dihydro-5-chloro-1,3,3-trimethyl-6′-(p-diethylamino)phenylspiro[2H-indole-2,3′-[3H]naphth[2,1-b][1,4]oxazine]. (Formula VIII).

mp 217°–8° C.

Absorbance: $\lambda_{max}$ 620 nm(PU)

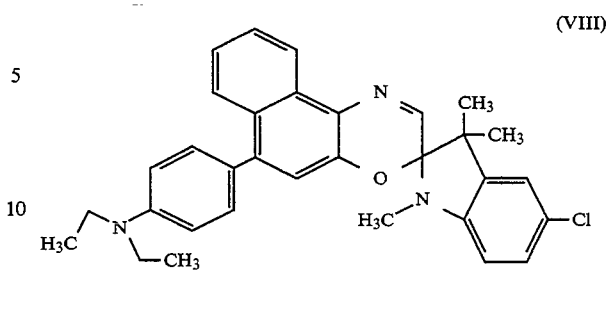

EXAMPLE 5

1,3-dihydro-5-methoxy-1,3,3-trimethyl-6′-(p-diethylamino)phenylspiro[2H-indole-2,3′-[3H]naphth[2,1-b][1,4]oxazine]. (Formula IX).

mp 202°–3° C.

Absorbance: $\lambda_{max}$ 648 nm(PU)

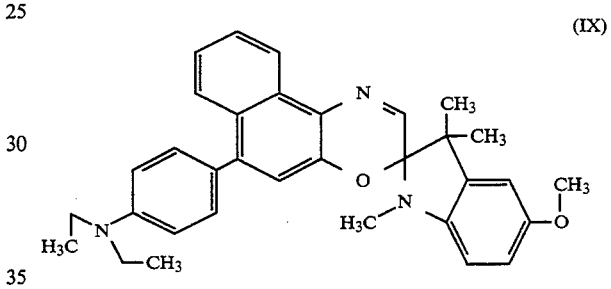

EXAMPLE 6

1,3-dihydro-1,3,3-trimethyl-6′-(p-diethylamino)phenyl spiro[2H-benz[e]indole[2,3′-[3H]naphth[2,1-b][1,4]oxazine]. (Formula X).

mp 207-15° C.

Absorbance: $\lambda_{max}$ 648 nm(PU)

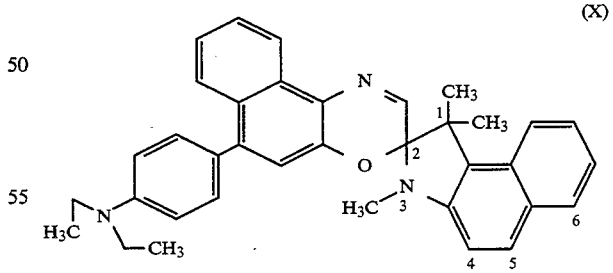

EXAMPLE 7

1,3-dihydro-3,3-dimethyl-1-neopentyl-6′-(p-diethylamino)phenylspiro[2H-indole-2,3′-[3H]naphth[2,1-b][1,4]oxazine]. (Formula XI).

mp 188°–191° C.

Absorbance: $\lambda_{max}$ 626 nm(PU)

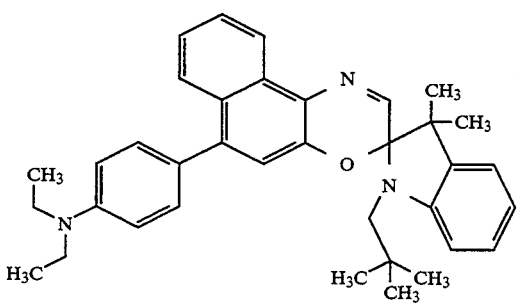

(XI)

EXAMPLE 8

1,3-dihydro-5-methoxy-1,3,3-trimethyl-6'-(1,1-bis [p-dimethylaminophenyl]ethylen-2-yl)spiro[2H-indole-2,3'-[3H]naphth[2,1-b][1,4]oxazine. (Formula XII).

Absorbance: $\lambda_{max}$ 670 nm(PU)

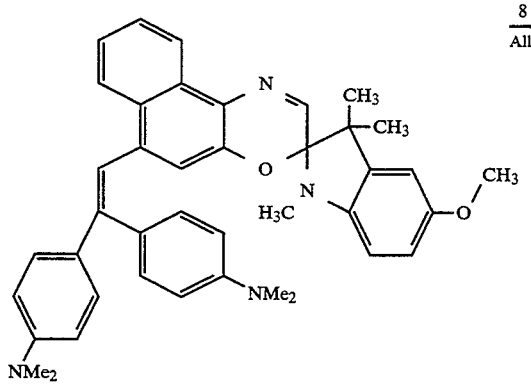

EXAMPLE 9

1,2,5,6-Tetrahydro-1,1,4-trimethyl-6'-(p-diethylamino) phenyl-spiro[4H-pyrrolo[3,2,1-ij]quinoline-2,3'-[3H]naphth [2,1-b][1,4]-oxazine. (Formula XII).

mpt 216°–224° C.

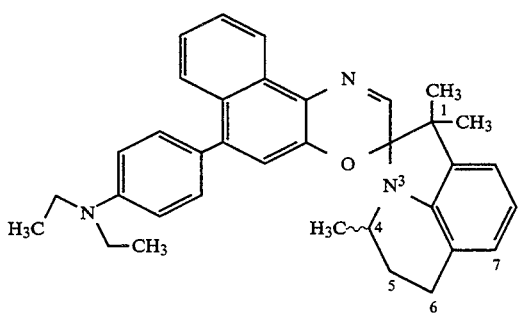

The photochromic compounds prepared in Examples 1,5,6 and 8 were each individually incorporated into a polyurethane host to prepare laminates in order to determine the properties of the photochromic materials. The results in Table I below include the integrated visible transmission of the lens (IVT) in both the Faded or bleached state and the darkened state. These values show the visual photochromic range which can be achieved, and show the suitability of the material for use in sun-lenses and car rooflights. The values for $\lambda_{max}$ demonstrate that a number of the compounds show significant absorbance in the infra-red region of the spectrum, and hence can be used in laminates in applications such as car rooflights and architectural windows where there is a need For control heat transmission. The change in a,b values on darkening is also given, and the induced optical density. The induced optical density (IOD) is:

$$IOD = \text{Log}_{10} \frac{BT}{DT}$$

where BT and DT are bleached and darkened transmission at the point of maximum absorbtion of the chromophore. The a,b values illustrate the green colour of the compounds.

TABLE I

| Ex | λ max | Bleached IVT | *a | *b | Darkened IVT | a* | *b | IOD |
|---|---|---|---|---|---|---|---|---|
| 1 | 626 | 87.70 | −7.68 | 11.60 | 48.19 | −28.30 | −20.57 | 0.26 |
| 5 | 648 | 81.0 | −10.3 | 20.9 | 53.7 | −24.3 | −8.2 | 0.18 |
| 6 | 648 | 84.7 | −10.7 | 12.0 | 37.8 | −40.6 | −20.9 | 0.35 |
| 8 | 670 | 78.4 | −17.7 | 49.3 | 53.0 | −12.3 | 11.3 | 0.17 |

All samples 0.2% w/w in polyurethane (1 mm) laminates.

We claim:

1. Photochromic compounds comprising a structure which includes a spiropyrrolidinebenzoxazine structure comprising a pyrrolidine part and a benzoxazine part and the benzoxazine part includes at least one mesomeric electron donating group chosen from amino and alkoxy moieties, the at least one mesomeric electron donating group being linked to a 6'-position of the benzoxazine part such that said compound is fully conjugated in a ring-opened state and said compound exhibits a green colour in a darkened condition.

2. Photochromic compounds as claimed in claim 1 in which the conjugated system includes at least one aromatic or heterocyclic ring.

3. Photochromic compounds as claimed in claim 1 or 2 which have a structure where the pyrrolidone part is annulated with a carbocyclic ring chosen From benzene and naphthalene and the structures are respectively spiroindolinebenzoxazine and spirobenzindoline benzoxazine.

4. Photochromic compounds as claimed in claim 1 or 2 where the pyrrolidine part is annulated with a heterocyclic moiety.

5. Photochromic compounds as claimed in any of claims 1 to 4 in which the benzoxazine portion contains a carbocyclic or heterocyclic moiety fused at the 7'8' position.

6. Photochromic compounds as claimed in claims 3, 4 or 5, in which a bridge is established between the $N_1$ position on the pyrrolidine part and the annulated moiety.

7. Photochromic compounds as claimed in claim 1 having the structure of formula I (I)

wherein
- R¹ is a group selected from aryl, heteroaryl, heterocyclic, alkenyl, alkenylaryl, cycloalkenyl, cycloalkenylaryl, alkynyl, alkynylaryl, iminoaryl and azoaryl Forming a linkage to at least one amino or alkoxy group;
- R² is a group selected from hydrogen, alkyl, alkoxy, aryl, heteroaryl or amino;
- R³ are independent and are selected from C1 to C10 branched or linear alkyls, carbocyclic or heterocyclic rings or together form part of a carbocyclic or heterocyclic ring;
- R⁴ is a group selected from hydrogen, alkyl, alkoxy, alkenyl, alkynyl, imino, azo, amino, carboxy ester, amide, cyano, halogen, trifluormethyl, nitro, aryl or heteroaryl;
- R⁵ is a group selected from C1 to C20 alkyls either branched, linear or alicyclic, alkenyl, alkynyl, alkoxyalkyl, aryl, alkylaryl, heteroaryl or alkylheteroaryl;
- Z when present represents a carbocyclic or heterocyclic moiety; and
- Y when present is a carbocyclic or heterocyclic moiety.

8. Photochromic compounds as claimed in claim 7 having a structure as shown in formula II:

(II)

wherein R₁, R₂, R₃, R₄, Z and Y are as defined as claimed in claim 7 and X forms a heterocyclic moiety.

9. Photochromic compounds as claimed in claim 7 having the structure shown in formula III (III)

where R₁ is selected from where Ar indicates the point of attachment to the oxazine part of the structure, and R₅ is selected from C₁-C₁₈ branched or linear alkyls.

10. Photochromic compounds as claimed in claim 9 wherein R₅ is methyl, ethyl, isobutyl or neopentyl.

11. Photochromic compounds as claimed in claim 7 having the structure shown in formula IV (IV)

where R₁ is as defined in claim 7.

12. 1,3-dihydro-1,3,3-trimethyl-6'-(p-diethylamino)-phenyl spiro[2H-indole-2,3'-[3H]naphth[2,1-b] [1,4]oxazine].

13. 1,3-dihydro-3,3-dimethyl-1-neopentyl-6'-(p-dimethylamino)phenylspiro[2H-indole-2,3'[3H]naphth[2,1-b][1,4]oxazine].

14. 1,3-dihydro-1,3,3-trimethyl-6'-(1,1-bis[p-dimethylaminophenyl]ethylene-2-yl)spiro[2H-indole-2,3'-[3H]naphth[2,1-b][1,4]oxazine].

15. 1,3-dihydro-5-chloro-1,3,3-trimethyl-6'-(p-diethyl-amino)phenylspiro[2H-indole-2,3'-[3H]naphth[2,1-b][1,4]-oxazine].

16. 1,3-dihydro-5-methoxy-1,3,3-trimethyl-6'-(p-diethylamino)phenylspiro[2H-indole-2,3'-[3H]naphth[2,1-b][1,4]oxazine].

17. 1,3-dihydro-1,1,3-trimethyl-6'-(p-diethylamino)-phenylspiro[2H-benz[e]indole[2,3'-[3H]naphth[2,1-b][1,4]oxazine].

18. 1,3-dihydro-5-methoxy-1,3,3-trimethyl-6'-(1,1-bis[p-dimethylaminophenyl]ethylen-2-yl)spiro[2H-indole-2,3'-[3]naphth[2,1-b][1,4]oxazine].

19. 1,2,4,5-Tetrahydro-1,1,4-trimethyl-6'-(p-diethyl amino)phenyl-spiro[4H-pyrrolo[3,2,1-ij]quinoline-2,3'[3H]naphth[2,1-b][1,4]-oxazine].

20. Photochromic compounds as claimed in claim 4, in which a bridge is established between the N₁ position on the pyrrolidine part and the annulated moiety.

* * * * *